US008242323B2

(12) United States Patent
Jain et al.

(10) Patent No.: US 8,242,323 B2
(45) Date of Patent: Aug. 14, 2012

(54) DETOXIFICATION OF CHEMICAL AGENTS

(76) Inventors: Ravi Jain, Bridgewater, NJ (US); Abhinav Jain, Bridgewater, NJ (US)

( * ) Notice: Subject to any disclaimer, the term of this patent is extended or adjusted under 35 U.S.C. 154(b) by 597 days.

(21) Appl. No.: 11/981,079

(22) Filed: Oct. 31, 2007

(65) Prior Publication Data

US 2009/0112044 A1 Apr. 30, 2009

(51) Int. Cl.

| | |
|---|---|
| ***B09B 1/00*** | (2006.01) |
| ***B09B 3/00*** | (2006.01) |
| ***B09B 5/00*** | (2006.01) |
| ***A62D 3/38*** | (2007.01) |
| ***C02F 1/72*** | (2006.01) |
| ***A61L 2/00*** | (2006.01) |
| ***A61L 2/18*** | (2006.01) |
| ***A61L 9/00*** | (2006.01) |

(52) U.S. Cl. ..................... 588/320; 588/249.5; 588/406; 588/407; 588/408; 588/413; 210/758; 210/759; 422/28

(58) Field of Classification Search .................. 210/758, 210/759, 762, 908, 909; 252/186.1; 422/28; 423/437.1; 588/200, 204, 206, 207, 208, 588/213, 226, 302, 313, 320

See application file for complete search history.

(56) References Cited

U.S. PATENT DOCUMENTS

| | | | | |
|---|---|---|---|---|
| 5,746,926 | A * | 5/1998 | Ross et al. | 210/761 |
| 6,080,906 | A * | 6/2000 | Johnson et al. | 435/262.5 |
| 6,498,281 | B1 * | 12/2002 | Lupton | 588/309 |
| 2003/0158459 | A1 * | 8/2003 | Tucker | 588/200 |
| 2009/0112044 | A1 * | 4/2009 | Jain et al. | 588/320 |

* cited by examiner

*Primary Examiner* — Stanley Silverman
*Assistant Examiner* — Jennifer Smith
(74) *Attorney, Agent, or Firm* — Ash Tankha; Lipton, Weinberger & Husick

(57) ABSTRACT

This invention provides a process for the detoxification of chemical agents including chemical warfare agents such as sulfur mustards, nitrogen mustards, nerve agents of G and V type, lewisite and adamsite by reacting the chemical agents with hydroxyl radicals at a pH greater than 7.0 to detoxify the agents and to render them suitable for disposal. The process can be used on-site and can be easily scaled to fairly large sizes.

35 Claims, 2 Drawing Sheets

DETOXIFICATION OF CHEMICAL AGENTS

FIELD OF THE INVENTION

The present invention is directed to a process for detoxifying chemical agents and more particularly to detoxifying chemical warfare agents and their neutralization products and render them suitable for disposal.

BACKGROUND OF THE INVENTION

Over the past several decades, various highly toxic chemical agents including chemical warfare agents (CWAs) have been developed and stockpiled by several nations. In January 1993, representatives from more than 130 nations signed the final draft of the Chemical Weapons Convention (CWC), which outlaws the production, use, sale, and stockpiling of all chemical weapons and their means of delivery and calls for the destruction of existing stocks. The CWC entered into force in April 1997. Out of an estimated 74,000 tons of CWAs contained in bulk storage vessels, metal barrels, canisters, rockets, landmines, mortar and artillery shells, cartridges, and missiles in the United States, former Soviet Union, and other countries about 24,000 tons have been destroyed as of July 2007 (www.opcw.org). While significant progress has been made, much work remains to be done. None of the countries met the original deadline and all have received extensions. The cost of disposal and objections from environmental groups to some of the technologies currently used for disposal remain barriers to the speedy disposal of CWAs.

The major CWAs fall into three main classes: sulfur mustards (HD and N), nitrogen mustards (HN1, HN2 and HN3), and organophosphorous nerve agents (acetylcholinesterase inhibitors) of the G (GA, GB, GD, GE, GF) and V (VX, VE, VG, VM) type. Additionally, lewisite (L) and adamsite have been produced in significant quantities.

It was decided by appropriate authorities that the method of choice in the United States for the disposal of chemical stockpiles would be by incineration because of the perceived low cost and the relative simplicity of incineration technology. However, it is becoming clear that incineration of chemical warfare agents poses risks of both an immediate and long term nature which may not be acceptable to the public. Public health and ecosystem integrity are threatened by the emission of materials which can escape the combustion train, resulting in uncharacterized products of incomplete combustion which are dispersed into the atmosphere. Less than 72 hours after start-up, the U.S. Army had to shut down its first domestic CWA destruction facility in Tooele, Utah, located in a sparsely populated region in the western United States, when the nerve agent Sarin was detected in an area outside the chamber in which Sarin-filled rockets were being destroyed.

Earlier public opposition to incineration led U.S. government authorities to consider alternative methods, including chemical treatment of the CWAs, capable of producing environmentally benign products. However, this concept was dismissed in the United States after publication in 1984 of a National Research Council report stating that, when compared to incineration, chemical neutralization processes "are slow, complicated, produce excessive quantities of waste that cannot be certified to be free of agent, and would require higher capital and operating cost." However, recently some of the chemical treatment methods such as neutralization with an alkali metal hydroxide have been used for detoxifying chemical weapons such as VX nerve gas.

Alternatives to incineration such as molten salt oxidation, supercritical water oxidation, reactions with various chemicals, electrochemical oxidation, neutralization, hydrolysis, biodegradation, steam-reforming, etc., have been proposed in the literature. This is not an exhaustive list. However, it does give an indication of the methods that have been proposed.

The chemical treatments proposed in the past for detoxifying chemical warfare agents have not been entirely satisfactory. For example, the treatments have not been applicable to the entire spectrum of chemical warfare agents. Most chemical reagents are species-specific; that is, a chemical reagent generally reacts with a substance having a certain specific functional group. With such species-specific chemistry, destruction of a CWA would require one to first establish the identity of the CWA or the mixture of CWAs to be destroyed in order to select the right reagent or combination of reagents to react with that particular material.

Chemical methods previously proposed for the destruction of chemical warfare agents are also believed to require unacceptable capital and labor costs. In view of this background, it is easy to understand that compared against such chemical treatments, incineration of the CWAs to produce water, carbon dioxide and inorganic salts, appears attractive. However, as discussed earlier, incineration has its own problems due to release of undesirable byproducts and other safety issues. This has led to a significant public opposition to incineration.

The need therefore exists for a treatment system that does not employ chemicals or equipment that are difficult or dangerous to transport. Unfortunately, existing chemical treatments for detoxification of chemical agents have significant drawbacks. Existing detoxification solutions are only effective against a certain class of agents. Also, use of existing decontaminants under inappropriate conditions can result in the formation of dangerous by-products.

Most chemical detoxification processes include some form of hydrolysis. Hydrolysis is accomplished by reacting CWAs with a base such as an alkali metal hydroxide. Hydrolysates are the reaction products of the reaction between the chemical agents and the base. Hydrolysis of CWAs creates intermediates or oxidation by-products of CWAs such as organophosphorous compounds that are sometimes more toxic than the agent itself. While hydrolysis may be acceptable for some organophosphorous compounds, it is not universally effective against all or even most CWAs.

These considerations highlight the need for a system capable of detoxifying a broad range of chemical warfare agents without producing toxic by-products. In addition, there is a need for a detoxification system that is compatible with most common materials, easy to dispense and environmentally safe. The present invention provides a simple and efficient method for achieving these objectives.

SUMMARY OF THE INVENTION

Accordingly, there is a need for a safer method and a method that is generally applicable for detoxifying and destroying a wide range of chemical agents with differing functional groups economically and with minimal effect on the environment and over a wide range of conditions.

Disclosed herein is a process for the treatment of chemical agents comprising reacting the chemical agents with hydroxyl radicals at a pH greater than 7.0 to detoxify the agents and to render them suitable for disposal.

Also, disclosed herein is a process for the treatment of a chemical agent comprising: (a) introducing the chemical agent in a reactor, (b) adding a base to the chemical agent in the reactor to increase the pH of the reactants in the reactor to greater than 7, (c) adding an oxidant to the reactor under basic pH conditions to generate hydroxyl radicals, (d) reacting the chemical agents and the hydroxyl radicals during the neutralization process, and (e) continuing the reaction till at least a portion of the chemical agent is detoxified.

Examples of chemical agents include chemical warfare agents such as sulfur mustards, nitrogen mustards, organophosphorous nerve agents, lewisite, adamsite, partially degraded CWAs as well as energetic materials such as TNT, RDX, nitroglycerine and their combinations. The method of this invention provides for the destruction of chemical agents including highly toxic CWAs, to generally produce substances of substantially less or substantially no toxicity. As used herein, the terms "destroying," "detoxifying", "degrading", "decontaminating" or the like as applied to chemical agents, for example chemical warfare agents means transforming the chemical agent into another chemical entity. The hydroxyl radicals as disclosed herein, unlike other species-specific reagents proposed for chemical warfare agents, act as powerful oxidizing agents with respect to most chemical agents including CWAs, converting them to non-toxic salts or other compounds which have a significantly lower toxicity than the chemical agents. The resulting reaction products are amenable to further treatment, if desired.

Disclosed herein is a method of detoxification of at least about 95 percent by weight of the chemical agent, often more than about 97%, and in favorable cases, more than 99% of the chemical agent. Under optimum conditions, the method of this invention can lead to detoxification of over 99.999 percent of the chemical agent.

In one embodiment, disclosed herein is a method for detoxifying chemical agents for example CWAs by hydroxyl radicals produced by the reaction of ozone, hydrogen peroxide and UV light or combinations thereof with a base such as an alkali metal hydroxide. Detoxification of chemical agents as well as neutralization and degradation products is contemplated.

In another embodiment, disclosed herein is a method for detoxifying chemical agents, for example CWAs that can not be neutralized by a base, such as an alkali metal hydroxide, by adding a base to the reactor and producing hydroxyl radicals using various combinations of ozone, hydrogen peroxide and UV light under basic pH conditions. Detoxification of chemical agents, neutralized degradation products, and non-neutralized degradation products is contemplated.

In another embodiment, disclosed herein is a method for detoxifying base neutralization products of chemical agents by adjusting the pH in the reactor to a basic pH, if needed, and producing hydroxyl radicals using ozone, or a combination of ozone and hydrogen peroxide. Detoxification of toxic chemicals, for example residual chemical agents and neutralization products is contemplated.

In all the embodiments disclosed herein, further treatment of degradation products by methods such as biological treatment or incineration is contemplated, if needed.

The methods to detoxify chemical agents disclosed herein can be used for major classes of chemical warfare agents including sulfur mustards (HD and N), nitrogen mustards (HN1, HN2 and HN3), organophosphorous nerve agents of the G (GA, GB, GD, GE, GF) and V (VX, VE, VG, VM) type, lewisite (L), and adamsite. The treatment methods disclosed herein are also applicable to energetic materials used in chemical weapons such as TNT, RDX and nitroglycerine as well as combinations of chemical weapons and energetic materials.

BRIEF DESCRIPTION OF THE DRAWINGS

The foregoing summary, as well as the following detailed description of the embodiments, is better understood when read in conjunction with the appended drawings. For the purpose of illustrating the invention, there is shown in the drawings exemplary constructions of the invention; however, the invention is not limited to the specific methods and instrumentalities disclosed herein.

DETAILED DESCRIPTION OF THE INVENTION

The term "chemical agent" as used herein includes any chemical compound including substantially pure chemical warfare agents, mixtures of chemical warfare agents (CWAs) in any proportions, chemical agents in impure states in which the other components are not CWAs, energetic materials used in the chemical weapons for explosive or propellant purposes, combinations of CWAs and energetic materials, etc. "Chemical warfare agents," as used herein, also includes partially or completely degraded CWAs, e.g., the gelled, polymerized, or otherwise partially or totally decomposed chemical warfare agents commonly found to be present in old munitions.

Representative chemical compounds against which the treatment system of the present invention is intended to detoxify include major classes of chemical warfare agents including sulfur mustards (HD and N), nitrogen mustards (HN1, HN2 and HN3), organophosphorous nerve agents of the G (GA, GB, GD, GE, GF) and V (VX, VE, VG, VM) type, lewisite (L), and adamsite. Energetic materials suitable for treatment by the methods of this invention include but are not limited to: TNT, RDX, HMX, Tetryl, Lead Azide, nitrocellulose, nitroglycerine, triacetin, dimethylphthalate, lead stearate, 2-nitrodiphenylamine, and combination energetic materials, etc. It will be appreciated, however, that the treatment system of the present invention may be effective for detoxification of other chemical agents in addition to those listed above.

Figure 1:
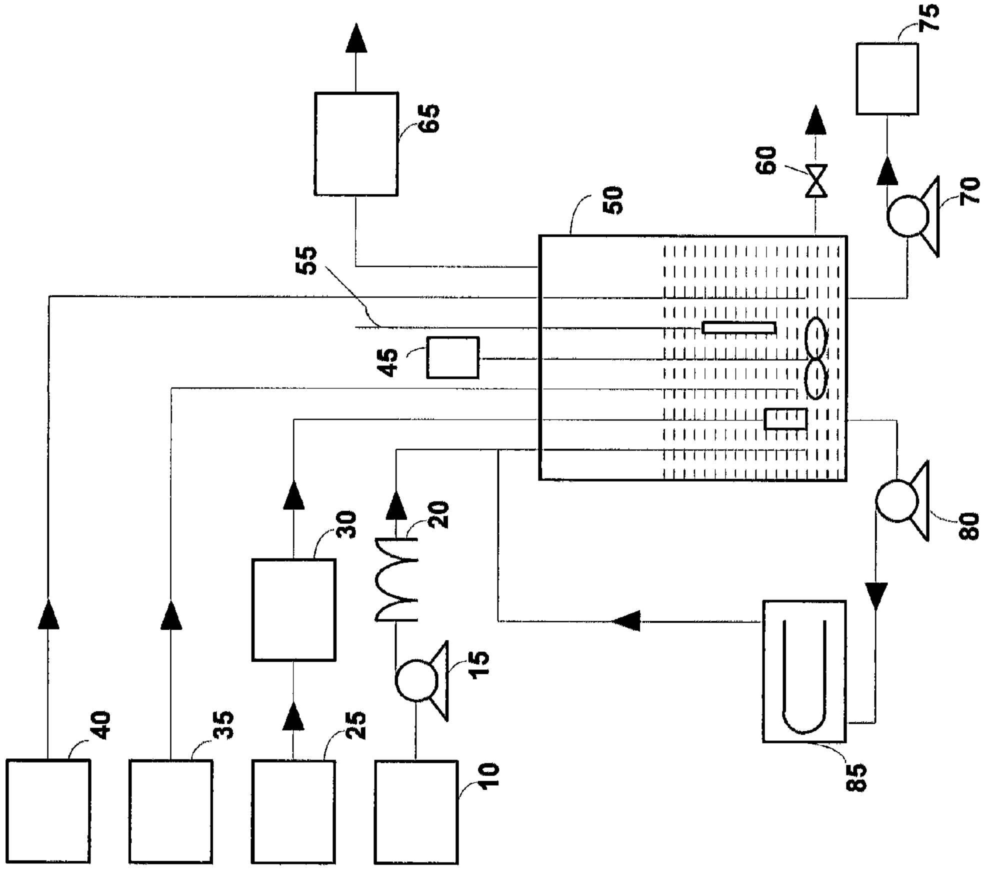
FIG. 1 is a schematic of the system for detoxifying chemical agents according to the present invention.

FIG. 1 shows chemical agents for example CWAs from source 10 transferred to a reactor 50 using a pump 15 and an optional heater 20. The source of chemical agents can be dismantled munitions or stockpile CWAs. Heater 20 is used if the reaction is to be carried out at a temperature higher than ambient. Reactor 50 also has the provision to introduce ozone, hydrogen peroxide and a base such as sodium hydroxide into the reaction mixture within the reactor 50. Ozone is produced using oxygen from source 25 and an ozone generator 30 and is then introduced into the reactor 50. While air, after drying, can be used for producing ozone it is much more efficient to use oxygen as the feed gas to the ozone generator to produce ozone. Oxygen in source 25 can be obtained from a liquid oxygen storage station, a pressure swing adsorption (PSA) oxygen generation system, or a vacuum swing adsorption (VSA) oxygen generation system. Ozone generator 30 would typically produce ozone using corona discharge and typical ozone concentrations are between approximately 6 and 16% by weight. Hydrogen peroxide is obtained from unit 35 which can provide hydrogen peroxide at concentrations between approximately 3 and 50% or higher. The base, for example, an alkali metal hydroxide such as sodium hydroxide, is obtained from unit 40. Unit 25 includes means to control oxygen flow to the ozone generator 30. Units 35 and 40 include means to control the flows of hydrogen peroxide and the base to reactor 50, respectively. Reactor 50 also includes a mixer 45 to rapidly mix the reactants and a sensor 55 to measure the pH of the reaction mixture within the reactor 50. Samples from reactor 50 can be removed using valve 60 and can be analyzed using various techniques such as high pressure liquid chromatography (HPLC) with a UV-VIS detector, or gas chromatography (GC) with flame ionization detector (FID) or flame photometric detector (FPD) for various components including chemical agents and degradation products. Both the GC and HPLC can be connected to a mass spectrometer to identify some of the unknown products formed during the reaction.

The reaction is started by introducing the chemical agents, for example CWAs to reactor 50 from source 10. Flow of ozone from generator 30 is started next. A base from source 40 is introduced into reactor 50 to maintain the pH greater than 7.0. The preferred pH range is approximately 8.0 to 14.0. At a pH higher than 7.0, hydroxyl radicals (OH.) are produced by the reaction of the oxidant, for example, ozone with the base such as sodium hydroxide according to the following, unbalanced, reaction:

$$O_3+OH^-\rightarrow OH.$$

The hydroxyl radicals oxidize and detoxify the chemical agents in reactor 50. As used herein, "reaction mixture" refers to the mixture of the chemical agent to be detoxified, oxidants such as ozone and hydrogen peroxide, and the base added to the chemical agent in the reactor.

Hydroxyl radicals have an oxidation potential of 1.9 volts and are a much stronger oxidant than ozone, oxygen and other oxidants. Reaction of hydroxyl radicals with the chemical agents, for example CWAs, and the neutralization products degrades the chemical agents to significantly less toxic products. While the hydroxyl radical is the primary oxidant, other ionic and radical species as well as the oxidants ozone and/or hydrogen peroxide in the reaction mixture would perform some of the detoxification.

Since conventional ozone generators cannot produce ozone at concentrations much higher than approximately 16% by weight, the amount of ozone that can be transferred to the reactor and the resulting formation of hydroxyl radicals can be limited. One way to overcome this limitation is to introduce hydrogen peroxide in the reactor in addition to ozone. Formation of hydroxyl radicals by ozone-hydrogen peroxide system occurs according to the following reaction.

$$H_2O_2\rightarrow HO_2^-+H^+$$

$$HO_2^-+O_3\leftrightarrow OH.+O_2.^-+O_2$$

As discussed earlier, hydrogen peroxide can be introduced into the reactor 50 from source 35. Flow of hydrogen peroxide from source 35 to reactor 50 would normally be controlled to maintain an adequate concentration of hydrogen peroxide in the reactor. The concentration of hydroxyl radicals in reactor 50 can be increased even further by passing its contents using pump 80 through an ultraviolet (UV) reactor 85. The UV reactor 85 has a UV source which provides UV radiation in approximately the 190 to 390 nm range. Decomposition of both ozone and hydrogen peroxide in the UV reactor produces additional hydroxyl radicals. The stream exiting the UV reactor 85 is returned to reactor 50.

While the reaction would normally be carried out at close to ambient pressure and temperature, it is possible to heat the reactants entering reactor 50, for example to a temperature of about 100° C. to increase the rate of reaction to increase the rate of reaction and complete the detoxification process faster. The reaction temperature is selected to minimize decomposition of ozone prior to reaction. Also, as in the case of ozone alone, hydroxyl radicals are the predominant source of oxidants for the reaction, but other species including other ionic and radical species as well as oxidants can also take part in the reaction to detoxify the chemical agents.

The gaseous exhaust from reactor 50 is treated in unit 65, if necessary, and is then vented. Unit 65 may be a catalytic oxidation unit, a combustion unit, a unit similar to reactor 50, an adsorption unit or any other unit that can remove non-desirable components from the exhaust stream. After a certain amount of time, as determined by the analysis of samples from the reactor 50, or by pH measurements, addition of ozone, the base and hydrogen peroxide to reactor 50 is stopped and the treated chemical agents are removed using pump 70 and are discharged to a downstream treatment unit 75. The treatment unit 75 can be a unit similar to reactor 50, a catalytic combustion unit, an adsorption unit, an incinerator (off-site, or on-site) or a biological treatment unit. If the reaction is carried out in reactor 50 for a period of time just sufficient to destroy the chemical agents including CWAs, and some of the degradation and neutralization products, the effluents from reactor 50 may have to be treated further using one of the methods outlined above. However, if the reaction is carried out for a sufficient period of time, the effluents from the reactor 50 may be non-hazardous and may be disposed off in a sanitary sewer or landfilled.

Once the reaction products from reactor 50 have been removed, the reactor can be charged again with chemical agents from source 10 and the base, ozone and/or hydrogen peroxide can be added as appropriate and the treatment cycle restarted. The treatment process is continued until the contents of source 10 are exhausted.

Figure 2:
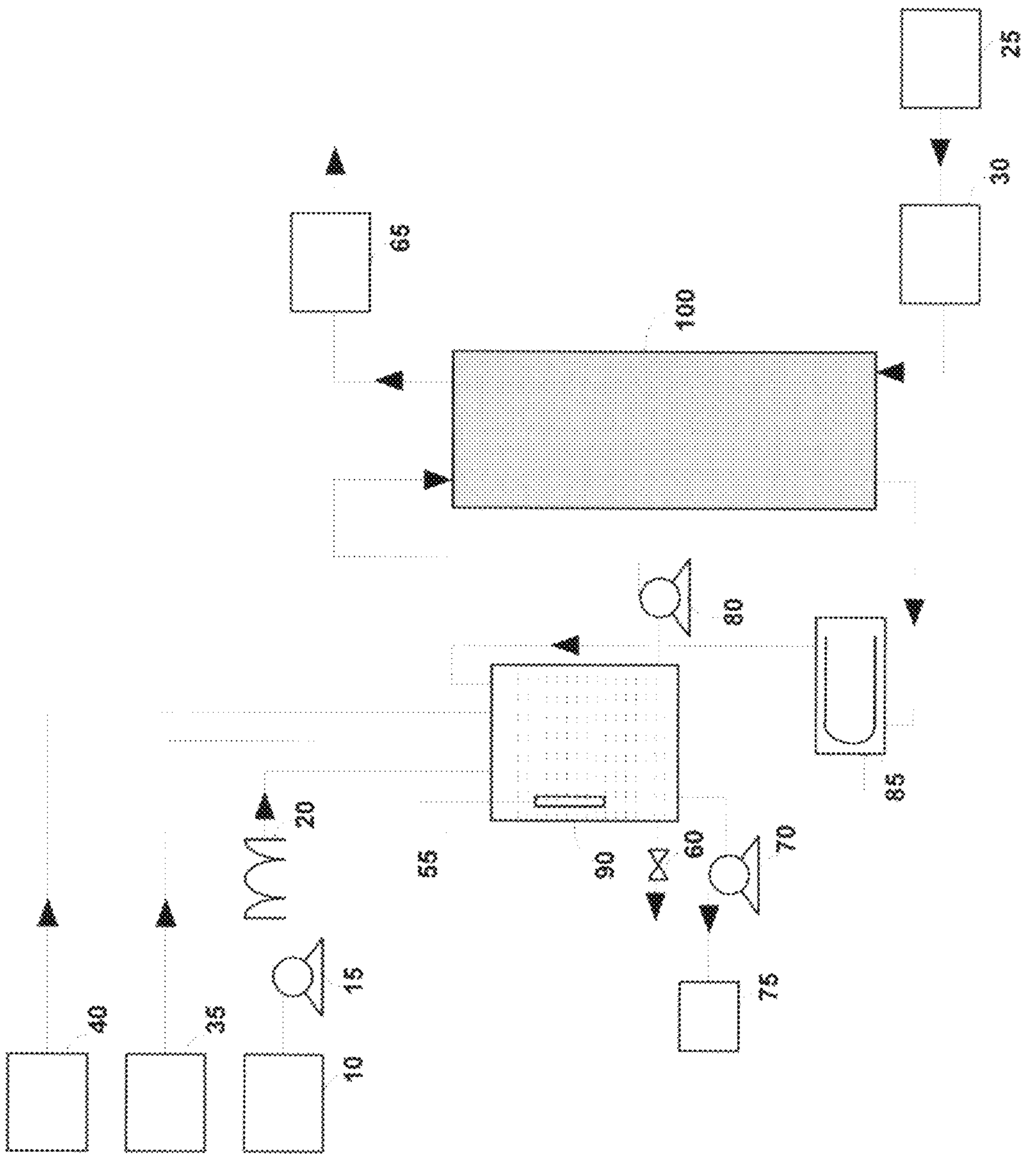
FIG. 2 shows additional reactor configurations to carry out the detoxification process according to the treatment methods disclosed herein.

Use of a different type of reactor is shown in FIG. 2. In FIG. 2, chemical agent such as CWAs from source 10, the base from source 40 and hydrogen peroxide from source 35 are transferred to a holding tank 90. This mixed stream is pumped using pump 80 and is sent to a reactor 100. Ozone produced using oxygen from source 25 and an ozone generator 30 flows in a direction countercurrent to the flow of liquid stream in reactor 100. Reactor 100 is a countercurrent contacting device as discussed below. Residual ozone along with gaseous reaction products from reactor 100 are treated in unit 65 and are exhausted. The operation of unit 65 has been described previously in relation to FIG. 1. The liquid stream exiting reactor 100 can be optionally passed through a UV reactor 85 and returned to the holding tank 90. Analysis samples can be withdrawn from tank 90 using valve 60. When the treatment is deemed complete, the contents of tank 90 are pumped to the treatment process 75 using pump 70. Operation of the treatment process 75 has been previously described with respect to FIG. 1.

Reactor 100 can be a packed column containing a structured or random packing. It can also be a membrane contactor wherein ozone stream flows on the shell or the tube side of the membrane contactor and the liquid stream flows on the opposite side. Packing and membrane materials need to be compatible with ozone, hydroxyl radicals, the base and hydrogen peroxide. Stainless steel (316) or fluorinated polymers are examples of suitable packing or contact materials. Some of the suitable materials for the membrane contactor include silicone rubber, teflon, amorphous Teflon, and PVDF.

Virtually all types of chemical agents can be treated by the methods of this invention, as will be apparent to those skilled in the art based on the present teachings. For the chemical weapon agents that can be neutralized by a base such as an alkali metal hydroxide, the system of this invention reacts with both the CWAs and their neutralization products thereby significantly speeding up both the neutralization and degradation. A possible mechanism for this involving CWAs, oxidant (OX), base (B), neutralization products (NP), degradation products (DPs) and waste products (WPs) is shown below.

CWA+OX→DP1

CWA+B→NP1

DP1+OX→DP2

NP1+OX→WP1

DP2+OX→WP2

DP2+B→NP2

NP2+OX→WP3

Some of the degradation products are converted to carbon dioxide and water in the presence of oxidants and would be removed in the gaseous effluent.

As seen in this reaction scheme, the hydroxyl radicals can oxidize not only the CWAs but also their neutralization products (NP1 and NP2) and their degradation products (DP1, DP2, etc). The degradation products in this reaction scheme may require further treatment whereas the waste products would require little or no further treatment. In some cases, if the reaction is carried out for a sufficient period of time, the final waste products may be non-toxic salts.

For chemical agents that can not be neutralized by a base (via an acid-base reaction), the method and system disclosed herein are still applicable. Even though no neutralization products are formed by the reaction of the base with CWAs, hydroxyl radicals produced under basic pH conditions will degrade CWAs and if any of the degradation products are acidic they would be neutralized by the base. The neutralization products can then be further degraded by the hydroxyl radicals. A possible reaction sequence for this case is shown below.

CWA+OX→DP1

DP1+OX→DP2

DP2+OX→DP3

DP2+B→NP1

DP3+OX→WP1

NP1+OX→WP2

Chemical agents including chemical warfare agents that have been stockpiled can be treated in accordance with the method and system disclosed herein. Specific examples of the chemical agents that can be advantageously treated in accordance with the present invention include, but are not limited to: major classes of chemical warfare agents including sulfur mustards (HD and N), nitrogen mustards (HN1, HN2 and HN3), organophosphorous nerve agents of the G (GA, GB, GD, GE, GF) and V (VX, VE, VG, VM) type as well as lewisite (L), and adamsite.

While this invention is directed to the treatment of chemical agents including chemical warfare agents, numerous types of energetic materials used in chemical weapons can be treated in accordance with the method and system disclosed herein. Such energetic materials include materials that are used for explosive or propellant purposes. Energetic materials which can be advantageously treated by the present methods and systems include, but are not limited to: TNT, RDX, HMX, Tetryl, Lead Azide, nitrocellulose, nitroglycerine, triacetin, dimethylphthalate, lead stearate, 2-nitrodiphenylamine, and combination energetic materials. The energetic materials can be combined with CWAs and treated in the same reactor or they can be treated in a separate reactor.

U.S. Pat. No. 5,430,228 to Ciambrone et al. describes a transportable ozone neutralization system for neutralizing a chemical compound such as a chemical weapon. The neutralization system of this patent refers to detoxification of chemical warfare agents and not to the chemical neutralization process involving an acid and a base. There is no teaching of using ozone at a basic pH, using ozone in combination with hydrogen peroxide and/or UV radiation. Since ozone is a selective oxidant many byproducts, some that may be fairly toxic, are likely to result from the use of the teachings of this invention. As discussed in Example 1 below, ozonation of malathion, a VX nerve gas analog, results in formation of more than 10 byproducts some of which such as malaoxon are more toxic than malathion. Also, the reaction rates with ozone alone are not very fast which may require several hours for appropriate detoxification of CWAs.

U.S. Pat. No. 6,498,281 to Lupton et al. describes a chemical munition hydrolysate treatment system in which the agent hydrolysate is treated with a photosensitizable oxidant to destroy the hydrolysate. The hydrolysate in this patent refers to the reaction products of reaction between the CWAs and a base such as sodium hydroxide. The invention requires two separate processes for the detoxification of CWAs: neutralization of CWAs with a base in a first process and the treatment of neutralization products (hydrolysate) in a second process and associated transfer of hazardous and toxic materials from one process to the other. The process of this invention also does not benefit from the synergistic combination of oxidation during neutralization which not only speeds up neutralization (by further degradation of neutralization products by hydroxyl radicals) but also speeds up degradation of neutralization products as well as degradation products of CWAs. Being able to treat the CWAs in a single step is a significant benefit as this avoids a number of steps involved in transferring CWAs from one treatment equipment to another. It also eliminates the environmental hazards associated with the shipment of hydrolysate for off-site treatment. The present invention provides such a process.

The process of this invention uses chemicals which are readily available for example, hydrogen peroxide and alkali metal hydroxide, or can be easily produced on-site, for example ozone from oxygen. None of these chemicals pose significant environmental hazards. Also, since commercial ozone generators can produce ozone at flow rates of up to approximately 6,000 kilograms per day, the process can be easily scaled to fairly large sizes, if needed.

While this invention discloses the treatment of toxic chemical agents for example chemical warfare agents, the process of this invention is also applicable to the treatment of hydrolysates produced by neutralization. A typical example of a hydrolysate produced by the reaction between CWAs and a base involves the reaction between the VX nerve agent and sodium hydroxide. The two main products of this reaction are sodium 2-(diisopropylamino)ethanethiolate and sodium ethylmethylphosphonate. The pH of the hydrolysates would need to be increased to over 8.0, if necessary, and then either ozone or ozone in combination with hydrogen peroxide and optionally UV light can be used to produce hydroxyl radicals needed for destroying residual chemical agents including CWAs and organic compounds in the hydrolysate.

The hydrolysate treatment process is suitable for the treatment of nerve agents such as GA, GB, GD, and VX and other agents such as HD, HN1, HN2, HN3 and lewisite.

By employing the method and system disclosed herein, at least about 95 percent by weight of the chemical agent, often more than about 97%, and in favorable cases, more than 99% of the chemical agent is detoxified. Under optimum conditions, the method of this invention can lead to detoxification of over 99.999 percent of the chemical agent.

Since very few places are equipped to do testing with actual chemical agents such as chemical warfare agents, a commonly used method to test processes for detoxifying chemical weapons is to use analogs or surrogates of chemical warfare agents. Many of these surrogates are commonly used pesticides. A commonly used pesticide, malathion, is an analog for the VX nerve gas. All the tests described in the Examples below were done with commercially available malathion.

Example 1

A 400 ml solution containing 0.1% malathion by volume (0.8 ml of Spectracide brand malathion containing 50% malathion) was vigorously stirred in a 500 ml reactor. An oxygen-ozone mixture containing about 10% ozone by weight was bubbled into the reactor at a rate of 0.4 normal liters/min (normal conditions refer to 0° C. and 1 atmosphere). The reaction was monitored by taking the samples periodically and monitoring the pH of the reaction. The reaction products were analyzed using a Hitachi HPLC (with L-4200H UV-VIS detector) containing a Varian Pursuit XRs 5u C18 column (250×4.6 mm). More than 10 reaction products were seen during the reaction period of four hours. Two of the reaction products were identified as malaoxon (about 70 times more toxic than malathion) and diethyl succinate. Malaoxon was seen after 15 minutes, reached its peak around 3 hours and had a concentration of about ⅓ its peak concentration after 4 hours. Diethyl succinate was seen after 45 minutes, reached its peak around 3 hours and after 4 hours its concentration was more than 50% of its peak concentration. Malathion concentration decreased steadily during the reaction. However, even after 4 hours more than 5% of malathion was still left in the reaction mixture. During the reaction period of four hours the pH of the reaction mixture decreased from 4.21 to about 2.68 indicating formation of acidic products during reaction with ozone.

This Example illustrates that while ozone alone at an acidic pH can destroy the chemical agents, it may require a long time to destroy all the chemical agents and the degradation products.

Example 2

The same mixture as in Example 1 (0.1% malathion by volume) was vigorously stirred in the reactor. Again an oxygen-ozone mixture containing about 10% ozone by weight was bubbled into the reactor at a rate of 0.4 normal liters/min. Two separate experiments were run. In one case, the pH of the reaction mixture was maintained at close to about 10.0 using 6M NaOH, and in another case the pH of the reaction mixture was maintained at close to about 12.0 using 6M NaOH solution. Again the reaction products were analyzed using the Hitachi HPLC.

In both the experiments, a smaller number of reaction products than in Example 1 were formed. The concentrations of the degradation products such as malaoxon were generally less than 1/10th of those in Example 1.

For the pH 10 case, malaoxon concentration peaked around 70 minutes and it was removed to below detection limit in less than four hours. Malathion was completely removed in less than three hours. After four hours a single peak was seen in the chromatogram and it was identified to be sodium oxalate, a non-toxic salt. It is possible that the reaction products contained other compounds such as sodium sulfate that were not identified by HPLC.

For the pH 12 case, malathion was removed to below detection limit in less than 80 minutes, and malaoxon was removed to below detection limit in less than 100 minutes. A single, sodium oxalate, peak was seen after two hours.

This Example illustrates that synergistic combination of neutralization with a base and oxidation with hydroxyl radicals can lead to rapid degradation of the chemical agent (malathion), the degradation products (such as malaoxon) and the neutralization products (converted to oxalate salt).

Example 3

A 400 ml of 0.1% malathion by volume solution was made by vigorously stirring 0.8 ml of Spectracide brand malathion containing 50% malathion and 3% hydrogen peroxide (CVS brand) in the reactor. Again an oxygen-ozone mixture containing about 10% ozone by weight was bubbled into the reactor at a rate of 0.4 normal liters/min. The pH of the reaction mixture was maintained at close to about 10.0 using 6M NaOH and the reaction products were analyzed using the Hitachi HPLC.

In this experiment, malathion was removed to below detection limit in less than twenty minutes, malaoxon was removed to below detection limit in less than 80 minutes and a single peak corresponding to the oxalate salt was obtained in less than 150 minutes.

Comparison of this Example with the pH 10 case of Example 2 illustrates that further increase in the concentration of hydroxyl radicals (through use of hydrogen peroxide) and synergistic combination of neutralization and oxidation with hydroxyl radicals can lead to a very rapid degradation of the chemical agent, the degradation products and the neutralization products.

Example 4

Commercial malathion products such as Spectracide malathion contain "inerts" and solvents such as xylenes in addition to malathion. Further experiments were done with malathion (>95% purity) obtained from Pfaltz and Bauer. Again 400 ml solutions of 0.1, 0.25 and 0.5% malathion by volume were made in 3% hydrogen peroxide. An oxygen-ozone mixture containing about 10% ozone by weight was bubbled into the reactor at a rate of 0.4 normal liters/min. The pH of the reaction mixture was maintained at close to 10.0 using 6M NaOH and the reaction products were analyzed using the Hitachi HPLC.

For 0.1, 0.25 and 0.5 volume % cases, single salt peaks were obtained in less than one hour, less than two hours and less than 2.5 hours, respectively. In all cases, malathion was destroyed to below detection limit in less than one hour. Removal of oxidant demand for "inerts" and solvents in this Example leads to faster degradation compared to Example 3. This Example also illustrates that fairly high concentrations of chemical agents can be treated by the method of this invention.

While the present invention has been described with reference to several embodiments and examples, numerous changes, additions and omissions, as will occur to those skilled in the art, may be made without departing from the spirit and scope of the present invention.

What is claimed is:

1. A process for the treatment of chemical agents comprising:

neutralizing the chemical agents by an acid-base reaction in a reactor to yield neutralization products by supplying an alkali metal hydroxide to said reactor;

producing hydroxyl radicals by reacting said alkali metal hydroxide with either ozone, or ozone in combination with hydrogen peroxide in said reactor at a pH greater than 7.0;

reacting chemical agents not neutralized by said acid-base reaction with said hydroxyl radicals to detoxify the chemical agents and to yield degradation products;

reacting the neutralization products and the degradation products with the hydroxyl radicals to increase the rate of neutralization and to further degrade the neutralization products, wherein steps of neutralizing the chemical agents, detoxifying the chemical agents by hydroxyl radicals, and further degrading the neutralized products are performed simultaneously within said reactor; and maintaining the pH over 7.0 in the reactor by continuous addition of alkali metal hydroxide to ensure continued neutralization and hydroxyl radical generation;

whereby simultaneously neutralizing the chemical agents and reacting the chemical agents and the neutralization products with the hydroxyl radicals renders them suitable for disposal.

2. The process of claim 1 wherein the disposal means for the treated chemical agent comprise catalytic oxidation, incineration, landfilling or biological treatment.

3. The process of claim 1 wherein effluent gases from the reaction are treated in a catalytic oxidation unit, a combustion unit, a reactor which brings the effluent gases in contact with hydroxyl radicals, or an adsorption unit.

4. The process of claim 1 wherein the chemical agents include chemical warfare agents are selected from the group consisting of sulfur mustards, nitrogen mustards, and organophosphorous nerve agents of the G and V type as well as lewisite (L), and adamsite.

5. The process of claim 4 wherein the sulfur mustards include HD and N.

6. The process of claim 4 where said nitrogen mustards include HN1, HN2 and HN3.

7. The process of claim 4 wherein the organophosphorous nerve agents of the G type include GA, GB, GD, GE, GF and the organophosphorous nerve agents of the V type include VX, VE, VG, VM.

8. The process of claim 1 wherein the chemical agents include energetic materials are selected from the group consisting of TNT, RDX, HMX, Tetryl, lead azide, nitrocellulose, nitroglycerine, triacetin, dimethylphthalate, lead stearate, 2-nitrodiphenylamine, and combination energetic materials.

9. The process of claim 1 wherein the chemical agents include the combination of chemical warfare agents and energetic materials.

10. The process of claim 1 wherein the pH range is between approximately 9.0 and 14.0.

11. The process of claim 1 wherein at least about 95 percent by weight of the chemical agent, preferably more than about 97%, and most preferably, more than 99% of the chemical agent is detoxified.

12. The process of claim 1 wherein the treatment of the chemical agents is carried out at a temperature between about ambient and 100° C.

13. The process of claim 1 wherein the treatment of the chemical agents is carried out in a stirred tank reactor, a packed bed reactor or a membrane contactor.

14. A process for the treatment of a chemical agent comprising:

introducing the chemical agent in a reactor;

adding an alkali metal hydroxide to the chemical agent in the reactor to increase the pH of the reactants in the reactor to greater than 7.0;

adding an oxidant to the reactor under basic pH conditions to generate hydroxyl radicals by reacting the alkali metal hydroxide with the oxidant, wherein the oxidant is one of ozone, and a combination of ozone and hydrogen peroxide;

neutralizing the chemical agents by an acid-base reaction to yield neutralization products;

reacting the chemical agents not neutralized by said acid-base reaction with the hydroxyl radicals during the neutralization process to detoxify the chemical agents and to yield degradation products;

reacting the neutralization products and the degradation products with the hydroxyl radicals to increase the rate of neutralization and to further degrade the neutralization products, wherein steps of neutralizing the chemical agents, detoxifying the chemical agents by hydroxyl radicals, and further degrading the neutralized products are performed simultaneously within the reactor;

maintaining the pH over 7.0 in the reactor by continuous addition of alkali metal hydroxide to ensure continued neutralization and hydroxyl radical generation; and continuing the reaction until at least about 95 percent by weight of the chemical agent is detoxified.

15. The process of claim 14 wherein the reaction of ozone; or ozone and hydrogen peroxide with the alkali metal hydroxide results in the formation of the hydroxyl radicals.

16. The process of claim 14 wherein effluent gases from the reaction are treated in a catalytic oxidation unit, a combustion unit, a reactor which brings the effluent gases in contact with hydroxyl radicals, or an adsorption unit.

17. The process of claim 14 wherein the treated chemical agents are further treated in a catalytic combustion unit, an incinerator, or a biological treatment unit.

18. The process of claim 14 wherein the said chemical agents include chemical warfare agents are selected from the group consisting of sulfur mustards, nitrogen mustards, and organophosphorous nerve agents of the G and V type as well as lewisite (L), and adamsite.

19. The process of claim 18 wherein the sulfur mustards include HD and N.

20. The process of claim 18 where the nitrogen mustards include HN1, HN2 and HN3.

21. The process of claim 18 wherein the organophosphorous nerve agents of the G type include GA, GB, GD, GE, GF and the organophosphorous nerve agents of the V type include VX, VE, VG, VM.

22. The process of claim 14 wherein the said chemical agents include energetic materials are selected from the group consisting of TNT, RDX, HMX, Tetryl, lead azide, nitrocellulose, nitroglycerine, triacetin, dimethylphthalate, lead stearate, 2-nitrodiphenylamine, and combination energetic materials.

23. The process of claim 14 wherein the pH range is between 9.0 and 14.0.

24. The process of claim 14 wherein at least about 95 percent by weight of the chemical agent, preferably more than about 97%, and most preferably, more than 99% of the chemical agent is detoxified.

25. The process of claim 14 wherein the reaction is carried out at a temperature between ambient and 100.degree. C.

26. The process of claim 14 wherein the treatment of the chemical agents is carried out in a stirred tank reactor, a packed bed reactor or a membrane contactor.

27. A process for the treatment of a chemical agent comprising:

introducing the chemical agent in a reactor;

adding an alkali metal hydroxide to the chemical agent in the reactor to increase the pH to greater than about 10.0;

adding about 3% to about 50% by weight of hydrogen peroxide to the reactor;

adding about 6% to about 16% by weight of ozone to the alkali metal hydroxide in the presence of the hydrogen peroxide in the reactor to generate hydroxyl radicals;

reacting the chemical agent with the hydroxyl radicals simultaneously during a neutralization process;

maintaining the pH over 7.0 in the reactor by continuous addition of alkali metal hydroxide to ensure continued neutralization and hydroxyl radical generation; and continuing the reaction until at least about 95 percent by weight of said chemical agent is detoxified.

28. The process of claim 27 wherein effluent gases from the reaction are treated in a catalytic oxidation unit, a combustion unit, a reactor which brings the effluent gases in contact with hydroxyl radicals, or an adsorption unit.

29. The process of claim 27 wherein the treated chemical agent is further treated in a catalytic combustion unit, an incinerator, or a biological treatment unit.

30. The process of claim 27 wherein the said chemical agent includes chemical warfare agents are selected from the group consisting of GA, GB, GD, VX, HD, HN1, HN2, HN3 and lewisite.

31. The process of claim 27 further comprising combining the chemical agent with energetic materials are selected from the group consisting of TNT, RDX, HMX, Tetryl, Lead Azide, nitrocellulose, nitroglycerine, triacetin, dimethylphthalate, lead stearate, 2-nitrodiphenylamine, and combination energetic materials.

32. The process of claim 27 wherein the pH range is between 10.0 and 14.0.

33. The process of claim 27 wherein at least about 95 percent by weight of the chemical agent, preferably more than about 97%, and most preferably, more than 99% of the chemical agent is detoxified.

34. The process of claim 27 wherein the treatment of the chemical agents is carried out a temperature between ambient and 100° C.

35. The process of claim 27 wherein the treatment of the chemical agents is carried out in a stirred tank reactor, a packed bed reactor or a membrane contactor.

* * * * *